United States Patent [19]
Ronchi et al.

[11] Patent Number: 5,455,377
[45] Date of Patent: Oct. 3, 1995

[54] PROCESS TO PREPARE ALKANSULPHONAMIDES

[75] Inventors: Nello Ronchi, Milan; Edoardo Pallucca, Settimo; Daniele Tarallo, Segrate; Claudio Ornati, Milan, all of Italy

[73] Assignee: Oxon Italia S.p.A., Pero, Italy

[21] Appl. No.: 273,815

[22] Filed: Jul. 12, 1994

[30] Foreign Application Priority Data

Jul. 28, 1993 [IT] Italy ................................ MI93A1680

[51] Int. Cl.$^6$ ................................ C07C 303/38
[52] U.S. Cl. ................................ 564/98; 564/96
[58] Field of Search ................................ 564/98, 96

[56] References Cited

U.S. PATENT DOCUMENTS 4,994,483  2/1991  Oxford et al. ................... 514/415
5,166,431  11/1992  Sandler et al. ................... 564/98

*Primary Examiner*—Peter O'Sullivan
*Attorney, Agent, or Firm*—Young & Thompson

[57] ABSTRACT

A process to prepare alkansulphonamides of formula $RSO_2NR^1R_2$—wherein R is an alkyl group containing from 1 to 15 carbon atoms, or an alkyl group containing from 1 to 15 carbon atoms substituted by one or more chlorine or bromine atoms, and $R^1$ and $R^2$ are equal or different and may be hydrogen or an alkyl group containing from 1 to 15 carbon atoms—provides to treat an alkansulphonylhalide of formula $RSO_2X$—wherein X is chlorine, bromine or iodine—with a suitable quantity of a compound of formula $NHR^1R^2$, using as solvent for said treatment an aliphatic nitrile.

6 Claims, No Drawings

PROCESS TO PREPARE ALKANSULPHONAMIDES

BACKGROUND OF THE INVENTION

The present invention concerns an improved process—particularly convenient on an industrial level—for preparing alkansulphonamides.

There are known to be processes for preparing alkansulphonamides (general formula: $RSO_2NR^1R^2$, wherein R is an alkyl group, or an alkyl group substituted by one or more chlorine atoms, and $R^1$ and $R^2$ are equal or different and can be hydrogen or an alkyl group) starting from alkansulphonylchlorides (general formula $RSO_2X$, wherein X is chlorine, bromine or iodine), which are caused to react with primary or secondary amines, or even with ammonia. With such processes, the treatment is carried out in suitable solvents. Among these solvents, the first ones to be adopted were the various ether compounds, preferably cyclic ethers. The most widely used of said ethers is tetrahydrofuran. Other tested solvents have shown considerable drawbacks. In particular, the nitroalkans evidenced that the solubility of the reaction products strongly depended on the temperature, hence requiring complicated and costly intermediate filtering steps. The use of toluene led to considerably lower reaction yields, while benzene involved all the problem connected to the use in industry of cancerous substances. The use of tetrahydrofuran—as a solvent for this reaction—is therefore still prevailing.

With all these processes it has however been necessary, up to now, to start from industrial raw materials having a high degree of purity, so as to keep this latter at the high levels required for the final product.

It has now been discovered that raw materials having a lower degree of purity may equally well be used, in the treatment of alkansulphonylchlorides for preparing alkansulphonamides, by suitably resorting to solvents other than those already used up to date.

SUMMARY OF THE INVENTION

The object of the present invention is a process to prepare alkansulphonamides of formula $RSO_2NR^1R^2$—wherein R is an alkyl group containing from 1 to 15 carbon atoms, or an alkyl group containing from 1 to 15 carbon atoms substituted by one or more chlorine or bromine atoms, and $R^1$ and $R^2$ are equal or different and may be hydrogen or an alkyl group containing from 1 to 15 carbon atoms—by treating an alkansulphonylhalide of formula $RSO_2X$—wherein X is chlorine, bromine or iodine—with a suitable quantity of a compound of formula $NHR^1R^2$, characterized in that the solvent used for said treatment is an aliphatic nitrile.

Preferably, the solvent used in the preparation of methanesulphonamide is acetonitrile.

Since nitriles have generally higher boiling points than ethers the use of the solvents according to the invention allows to practically carry out the distillation and solvent removal steps at an unusually high temperature and operating under vacuum, which was not possible—or had anyhow not even been attempted—according to known technique. By operating in this way, together with the solvent also any impurities which may be present in the raw material are thereby eliminated: it is thus possible to use, without any problems, an industrial raw material having a degree of purity which is not particularly high, with the obvious advantages deriving therefrom on an industrial level.

Furthermore, acetonitrile is less inflammable than tetrahydrofuran, with evident advantages as far as safety of the treatments and simplicity of the installations in which such treatments are carried out.

Another remarkable and direct advantage of acetonitrile in respect of tetrahydrofuran is its lower selling price, which obviously makes it very interesting from the economic point of view.

DESCRIPTION OF THE PREFERRED EMBODIMENTS

The process according to the present invention provides for the discontinuous treatment of alkansulphonylhalides with amines, in aliphatic nitriles. The reaction vessel is filled with a solution of the amine, or of ammonia, into the nitrile used as a solvent. Generally one operates under atmospheric pressure, by stirring, at an almost ambient temperature. The reaction is exothermic, whereby the reaction vessel often needs to be kept refrigerated, so as to avoid general or local superheatings, as well as to favor the reaction from a thermodynamic point of view.

The addition of alkansulphonylhalide is generally carried out drop by drop, under strong stirring, so as to improve the mixing and guarantee a more uniform temperature in the reaction zone. One operates with an excess of amine (at least two tools of amine per one mol of alkansulphonylchloride) so as to block the hydrochloric acid formed during the reaction of nucleophilic substitution of chloride with amine. Thus, simultaneously with the reaction, the quaternary ammonium salt is formed. In many cases, said quaternary salt is insoluble in the reaction solvent (this applies in particular to the reaction with ammonia, wherein $NH_4Cl$ is produced) so as to go out of equilibrium and thereby favor the reaction even further. The insoluble salt can then be easily removed by filtration.

Once the reaction is completed, the product can be easily separated from the reaction zone by distilling the solvent, under vacuum and at a high temperature.

This allows to obtain products with a high degree of purity, which fully satisfy the common requirements for the marketing thereof.

EXAMPLES

To illustrate more clearly—by mere way of example—the characteristics of the invention and the modes to carry out the same, some examples are given hereinafter of the process according to the invention.

Example 1

270 g of acetonitrile, used as solvent, were saturated with gaseous ammonia for 15 minutes. 75 g of methanesulphonylchloride (0.655 mols) were then added simultaneously with gaseous ammonia, over a period of one hour, keeping the temperature between 20°–25° C., under stirring. After addition of the reagents, the reaction mixture was left under stirring for 30 minutes. The excess of ammonia was removed from the reaction mass. The precipitated ammonium chloride was filtered from the organic phase. Distillation was carried out at a reduced pressure (35–40 mmHg), up to a temperature of 140° C. in a boiler. 60.7 g of melted methanesulphonamide (97.4% yield) were obtained, and were isolated and ground. The product analysed by differential thermal analysis and by ultimate analysis, showed a purity of 99.2%, with a melting point equal to 87°–91° C.

Example 2

Example 1 was repeated, except that the solvent used was ethyl cyanide, instead of acetonitrile, and that 37.5 g of methanesulphonylchloride (equal to 0.328 mols) were added. 30 g of methanesulphonamide (97% yield) were obtained, with a melting point of the product equal to 87°–91° C.

Example 3

540 g of acetonitrile, used as solvent, were saturated with gaseous ammonia for 15 minutes. Gaseous ammonia and 70 g (equal to 0.528 mols) of ethanesulphonylchloride were then simultaneously added, in one hour, keeping the temperature between 20°–25° C., under stirring. After addition of the reagents, the reaction mixture was left under stirring, at the same temperature, for 30 minutes. The excess of ammonia was removed from the reaction mass and the ;precipitated ammonium chloride was filtered. Distillation was carried out at a reduced pressure (35–40 mmHg), up to 140° C. in the boiler, to remove the solvent. 57.4 g of ethanesulphonamide (99,6% yield) were obtained, with a melting point of 50°–56° C.

Example 4

Example 3 was repeated, except that 540 g of ethyl cyanide, instead of acetonitrile, were used as solvent. 56.9 g of ethanesulphonamide (98.9% yield) were obtained, with a melting point of 52°–56° C.

We claim:

1. Process to prepare alkansulphonamides of formula $RSO_2NR^1R^2$, wherein R is an alkyl group containing from 1 to 15 carbon atoms, or an alkyl group containing from 1 to 15 carbon atoms substituted by one or more chlorine or bromine atoms, and $R^1$ and $R^2$ are equal or different and may be hydrogen or an alkyl group containing from 1 to 15 carbon atoms, comprising treating an alkansulphonylhalide of formula $RSO_2X$, wherein X is chlorine, bromine or iodine, with a suitable quantity of a compound of formula $NHR^1R^2$, in an aliphatic nitrile solvent.

2. Process as in claim 1, in which the aliphatic nitrile used as solvent has the formula RCN, wherein R is methyl or ethyl.

3. Process as in claim 1, in which the aliphatic nitrile used as solvent is acetonitrile ($CH_3CN$).

4. Process as in claim 1, in which the aliphatic nitrile used as solvent is ethyl cyanide ($CH_3CH_2CN$).

5. Process as in claim 1, in which the aliphatic nitrile used as solvent is acetonitrile ($CH_3CN$) in order to obtain methanesulphonamide ($CH_3SO_2NH_2$).

6. Process as in claim 1, in which the aliphatic nitrile used as solvent is acetonitrile ($CH_3CN$), in order to obtain ethanesulphonamide ($CH_3CH_2SO_2NH_2$).

* * * * *